United States Patent [19]

Saito et al.

[11] Patent Number: 5,047,172

[45] Date of Patent: Sep. 10, 1991

[54] W-SUBSTITUTED, OPTICALLY ACTIVE ALKANOL ESTER DERIVATIVES

[75] Inventors: Shinichi Saito; Takashi Inukai; Hiromichi Inoue; Kazutoshi Miyazawa; Kouji Ohno, all of Yokohamashi; Makoto Ushioda, Kawasakishi, all of Japan

[73] Assignee: Chisso Corporation, Osakafu, Japan

[21] Appl. No.: 409,093

[22] Filed: Sep. 19, 1989

Related U.S. Application Data

[63] Continuation-in-part of Ser. No. 59,117, Jun. 3, 1987, abandoned, and a continuation-in-part of Ser. No. 83,830, Aug. 11, 1987, abandoned.

[30] Foreign Application Priority Data

Jun. 9, 1986 [JP] Japan .................................. 61-133269
Aug. 12, 1986 [JP] Japan .................................. 61-189127
Mar. 23, 1987 [JP] Japan .................................. 62-68629

[51] Int. Cl.$^5$ ...................... C09K 19/12; C09K 19/10; C09K 19/8
[52] U.S. Cl. ......................... 252/299.61; 252/299.65; 252/299.66; 544/238; 544/242; 560/62; 560/63
[58] Field of Search ...................... 252/299.01, 299.65, 252/299.61, 299.66; 544/238, 242, 333; 546/255, 258, 345, 346; 560/62, 63

[56] References Cited

U.S. PATENT DOCUMENTS

| | | | |
|---|---|---|---|
| 4,725,688 | 2/1988 | Taguchi et al. | 554/298 |
| 4,775,223 | 10/1988 | Yoshinga et al. | 350/333 |
| 4,834,904 | 5/1989 | Krause et al. | 252/299.01 |
| 4,911,863 | 3/1990 | Sage et al. | 252/299.65 |

OTHER PUBLICATIONS

Sage, Ian C. et al., "Liquid Crystal Compounds Mixtures & Devices", Publication WO87/05012, Aug. 27, 1987.

*Primary Examiner*—Robert L. Stoll
*Assistant Examiner*—Greg M. Sweet
*Attorney, Agent, or Firm*—Wenderoth, Lind & Ponack

[57] ABSTRACT

Novel compounds characterized by increased spontaneous polarization values as one of the important specific features required for ferroelectric liquid crystal compositions, a liquid crystal composition containing the same, and an optical switching element utilizing the composition as a liquid crystal. The compounds are expressed by the formula (I) or (I')

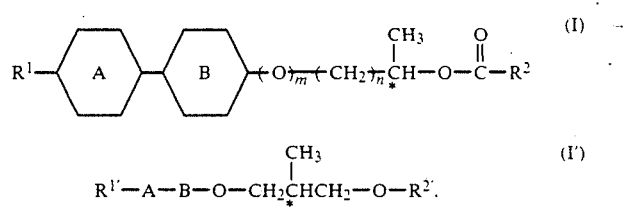

29 Claims, No Drawings

W-SUBSTITUTED, OPTICALLY ACTIVE ALKANOL ESTER DERIVATIVES

CROSS REFERENCE TO RELATED APPLICATIONS

This application is a continuation-in-part of both application Ser. No. 07/059,117 filed June 3, 1987, now abandoned and application Ser. No. 07/083,830 filed Aug. 11, 1987 now abandoned.

BACKGROUND OF THE INVENTION

1. Field of the Invention

This invention relates to a novel organic compound, a liquid crystal composition containing the same, and to an optical switching element utilizing the composition as a liquid crystal. More particularly, it relates to an organic compound having an optically active group and being useful as a component of ferroelectric liquid crystal compositions, a ferroelectric liquid crystal composition containing the same, and an optical switching element utilizing the composition as a liquid crystal.

2. Description of the Related Art

At present, TN (Twisted Nematic) type display mode has been broadly employed for liquid crystal display elements. This TN liquid crystal display has many advantages such as lower driving voltage, less power consumption, etc. However, the display element is inferior in the aspect of response speed to emissive type display elements such as cathode ray tube, electroluminescence, plasma display, etc. A new TN type display element having the twist angle increased from 90° as used in the conventional TN type liquid crystal display element to a range of 180° to 270° has also been developed, but it is still inferior in the aspect of response speed. As described above, various attempts for improvement have been made, but they have not yet been brought to practical use. Recently, however, a novel display mode using ferroelectric liquid crystals has been extensively researched, and according to such a mode, there is a possibility that the response speed is notably improved (Clark et al., Applied Phys. lett., 36, 899 (1980)). This mode is directed to a method of making use of chiral smectic phases such as chiral smectic C phase (hereinafter abbreviated to SC*) exhibiting ferroelectricity. Phases exhibiting ferroelectricity are not only SC* phase, alone, but it is known that chiral smectic phases of F, G, H, I, etc. also exhibit ferroelectricity.

Many specific features are required for practical use of ferroelectric liquid crystal materials in ferroelectric liquid crystal display elements, but at present there is no single compound which satisfies the requirements; hence, it is necessary to use a ferroelectric liquid crystal composition obtained by blending some liquid crystals or non-crystalline liquid crystal compounds.

Further, not only a ferroelectric liquid crystal composition consisting only of ferroelectric liquid crystal compounds, but also a ferroelectric liquid crystal composition has been proposed in Japanese patent application laid-open No. Sho 61-19518, which composition is obtained by blending at least one compound exhibiting a ferroelectric liquid crystal compound with compound(s) or a composition exhibiting an achiral smectic C, F, G, H, I or the like (hereinafter abbreviated to SC, SF, SG, SH, SI, etc., respectively) phase as basic substance(s) to give a ferroelectric liquid crystal composition as a whole. Still further, a ferroelectric liquid crystal composition has been reported in Mol. Cryst. Liq. Cryst., 89, 327 (1982), which composition is obtained by blending at least one compound which is optically active but exhibits no ferroelectric liquid crystalline phase with compound(s) or a composition exhibiting SC phase or the like as a main component to give a ferroelectric liquid crystal composition as a whole.

As a summary of these facts, it is seen that when at least one optically active compound, irrespective of whether or not this compound exhibits a ferroelectric liquid crystalline phase, is blended with smectic phase-exhibiting liquid crystal substance(s), it is possible to constitute a ferroelectric liquid crystal composition. Nevertheless, it is preferred that such an optically active substance also exhibit a liquid crystalline phase, and even when it exhibits no liquid crystalline phase, it is preferred to be a compound the structure of which is similar to those of liquid crystal compounds, so to speak a pseudo-liquid crystal substance.

SUMMARY OF THE INVENTION

The present inventors have found a compound characterized by increasing the spontaneous polarization value Ps as one of the important specific features required for the ferroelectric liquid crystal composition, and have attained the present invention.

In its first aspect, the present invention resides in an optically active compound expressed by the formula

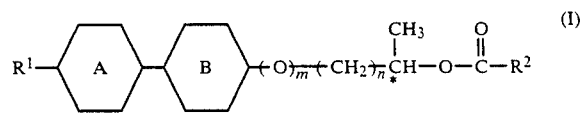

wherein $R^1$ represents a linear or branched chain alkyl group, alkoxy group, alkanoyl group, alkanoyloxy group, alkoxycarbonyl group, alkoxycarbonyloxy group or alkoxyalkyl group, each of 1 to 20 carbon atoms; $R^2$ represents hydrogen atom or a linear or branched chain alkyl group, alkoxy group or alkyl group substituted at ω-position thereof by halogen atom, cyano group, thioalkyl group, alkoxy group, alkanoyl group, alkanoyloxy group, alkoxycarbonyl group or alkoxycarbonyloxy group, each of 1 to 15 carbon atoms;

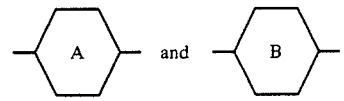

each independently represent

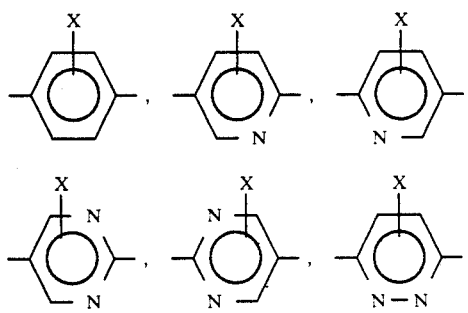

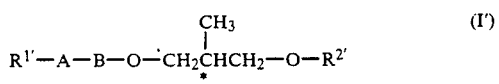

wherein X represents hydrogen atom, F atom, Cl atom, CN group, methyl group or trifluoromethyl group; m represents 0 or 1; n represents a natural number of 1 to 10; and the symbol * indicates that the carbon atom onto which the symbol * is attached is an asymmetric carbon atom, a ferroelectric liquid crystal composition containing the same, and to an optical switching element utilizing the composition as a liquid crystal.

In its second aspect, the present invention relates to an optically active compound represented by the formula $$R^{1'}-A-B-O-CH_2\overset{*}{\underset{|}{C}}HCH_2-O-R^{2'} \qquad (I')$$
$$\phantom{R^{1'}-A-B-O-CH_2}CH_3$$

wherein $R^{1'}$ represents an alkyl group having 1 to 20 carbon atoms or an alkoxy group having from 1 to 20 carbon atoms, $R^{2'}$ represents an alkyl group having from 1 to 15 carbon atoms, an alkanoyl group having from 2 to 15 carbon atoms, an alkoxycarbonyl group having from 2 to 15 carbon atoms, an alkoxyalkyl group having from 2 to 15 carbon atoms, an alkoxyalkanoyl group having from 3 to 15 carbon atoms, a halogenated alkyl group having from 1 to 15 carbon atoms or a halogenated alkanoyl group having from 2 to 15 carbon atoms, and the alkyl moiety in $R^{1'}$ and $R^{2'}$ is straight or branched; A and B each represents

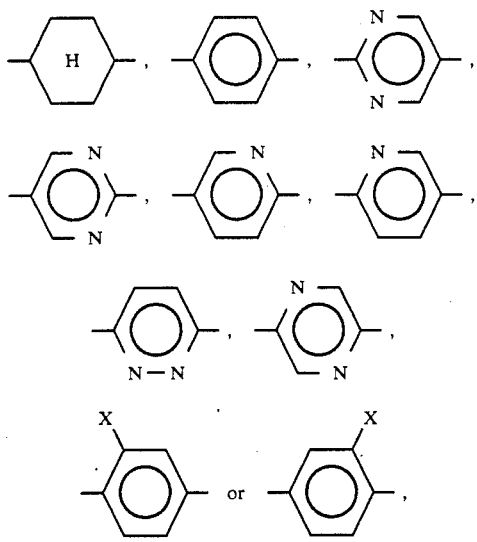

wherein X represents a halogen atom, a cyano group or a trifluoromethyl group; and the asterisk mark * indicates that the carbon atom provided with * is an asymmetrical carbon atom, a liquid crystal composition comprising at least one of the compounds represented by formula (I'), and particularly a ferroelectric liquid crystal composition, and an optical switching element using as a liquid crystal the liquid crystal composition comprising at least one of the compounds represented by formula (I').

DETAILED DESCRIPTION OF THE INVENTION

First Aspect of the Invention

Preferred examples of

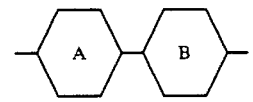

in the formula (I) are

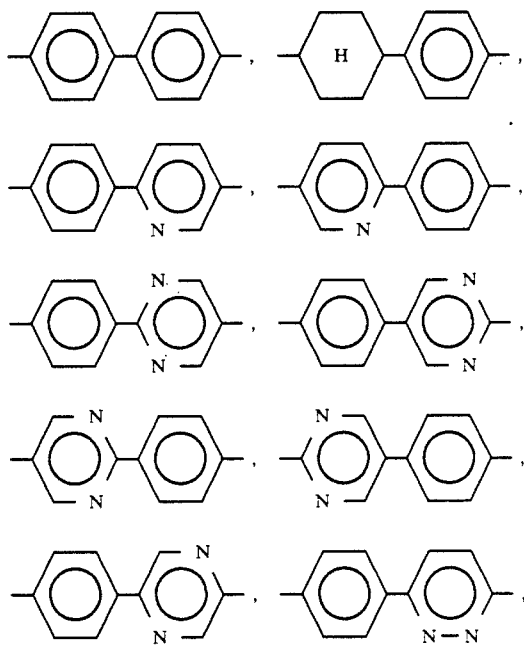

F-substituted, CN group-substituted and methyl group-substituted derivatives thereof, etc.

Preferred examples of $R^1$ are the groups as defined above but having 4 to 15 carbon atoms. When $R^1$ is a branched chain group and the presence of optically active form is possible, $R^1$ may be either in the optically active form or of course in the racemic form.

More preferred examples of $R^1$ are a linear or branched chain alkyl group or alkoxy group of 6 to 12 carbon atoms, and those which are linear or methyl group-branched are particularly preferred.

The $\omega$-substituted alkyl group in $R^2$ refers to a group expressed by the formula $-Y-CH_2-Z$ wherein Y represents a single bond or an alkylene group and Z represents a halogen atom, cyano group, a thioalkyl group, an alkoxy group, an alkanoyl group, an alkanoyloxy group, an alkoxycarbonyl group or an alkoxycarbonyloxy group.

Preferred examples of $R^2$ are an alkyl group, an alkoxy group and an $\omega$-substituted-alkyl group each of 1 to 8 carbon atoms, and when $R^2$ is a branched chain group and the presence of optically active form is possible, such a group may be those in optically active form and these often have superior specific features to those of a linear chain group. A more preferred example of $R^2$ is an alkyl group. m is preferably 1, n is preferably in the range of 1 to 6, more preferably 1 to 4.

The compound of the present invention itself is not always liquid crystalline, but when it is used as a component of ferroelectric liquid crystal compositions, it is possible to increase the spontaneous polarization value Ps of the compositions. Here, the importance of the spontaneous polarization Ps will be briefly described. In general, the response time $\tau$ in ferroelectric liquid crystal display elements is expressed by the following formula (II)

$$\tau = \frac{\eta}{Ps \cdot E} \quad (II)$$

wherein $\eta$ represents viscosity and E represents electric field strength.

As seen from the formula (II), reduction in the response time is effected by increasing Ps or reducing the viscosity.

The compound of the present invention, when used as a component of ferroelectric liquid crystal compositions, has a function of notably increasing the Ps of the ferroelectric liquid crystal compositions and as a result it is possible to reduce the response time. As described later in Examples, for example when a compound of the formula (I) of the present invention is added in an amount of 20% by weight to a liquid crystal composition exhibiting an achiral smectic C phase (which composition exhibits no spontaneous polarization), a ferroelectric liquid crystal composition having a large spontaneous polarization value is formed, and the response time exhibited by this composition is as short as 50$\mu$ sec. at 25° C. (Example 5). Further, when a compound of the formula (I) of the invention is added to a composition exhibiting chiral smectic C phase but having a very small Ps, it is possible to raise Ps up to a practical value (Example 6). In short, it can be said that the compound of the present invention is much superior as one contributing to improvement in Ps.

Further, since the compound of the formula (I) of the present invention has an optically active carbon atom, when it is added to a nematic liquid crystal, it has a capability of inducing a twisted structure in the resulting composition. Nematic liquid crystals having a twisted structure, i.e. chiral nematic liquid crystals, do not form the so-called reverse domain (dechiralization lines); hence it is possible to use the compound of the formula (I) as an agent for preventing the reverse domain from forming.

Further, when the compound of the present invention is added to a nematic liquid crystal composition, the resulting chiral nematic liquid crystal composition has a very flat or negative chiral pitch temperature characteristic, as shown in Example 9 mentioned later. As to most of the chiral substances currently used for adding to nematic liquid crystals, the higher the temperature, the longer the chiral pitch, whereas substances having such a characteristic that the higher the temperature, the shorter the chiral pitch have also been reported, and it has been known that such substances reduce the temperature dependency of the threshold voltage as an electrooptical characteristic of TN type display elements (see 33rd Applied Physics-Related Associated Lecture Meeting (1986, Spring), Collected Lecture Preliminary Manuscripts, Ip-G-7 (page 78) and JAPAN DISPLAY '86, Collected Lecture Preliminary Manuscripts, 8.3 (pages 286-289)).

Since the compound of the present invention has physical properties similar to those of the above substances, it is possible to reduce the temperature-dependency of the threshold voltage of a chiral nematic composition having the compound blended therein.

Further, apart therefrom, in the case of the so-called super TN type display where the twist angle is 180°-270° in the TN type displays, change of pitch due to temperature variation notably reduces the display grade, whereas in the case where a chiral nematic liquid crystal composition having the compound of the present invention blended therein is used in the super TN type display, it is possible to prepare an excellent super TN type display element according to which the display grade is not damaged by temperature change.

As described above, the compound of the present invention is also useful as a chiral component compound of chiral nematic compositions.

Here, a relationship between the compound of the present invention and a compound disclosed in Japanese patent application laid-open No. Sho 61-44845 as a prior application will be referred to. The above prior application discloses a general formula (I) including an astronomically large number of compounds, and the compound of the present invention might be formally included in the formula (I), but the specification of the prior application does not disclose the same compounds as those of the present invention, either concretely or in the form of divided formulas of the formula (I).

Further, the effectiveness of the compounds of the prior application as indicated therein consists in that the compounds are added to a nematic liquid crystal to induce the cholesteric phase in the resulting composition and thereby improve the temperature characteristics of its pitch. Thus, the above effectiveness has nothing to do with the ferroelectric liquid crystals which are the object of the present invention. Accordingly, it can be said that the compound of the present invention is not disclosed in the above-mentioned prior application.

Next, the preparation of the compound of the formula (I) will be described below.

The compound of the formula (I) may be prepared for example as illustrated in the following equations, using an $\omega$-substituted-optically active 2-alkanol as an intermediate:

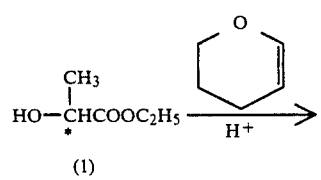

(1)

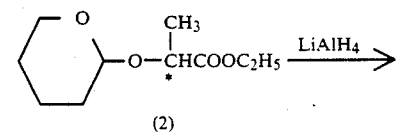

(2)

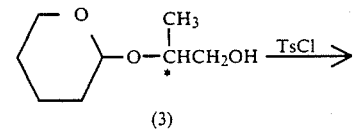

(3)

-continued

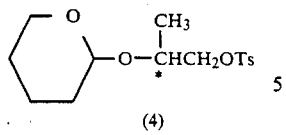
(4)

(a) When m = 0 and n = 1,

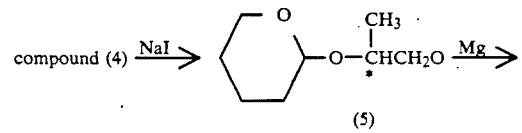
(5)

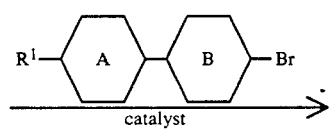

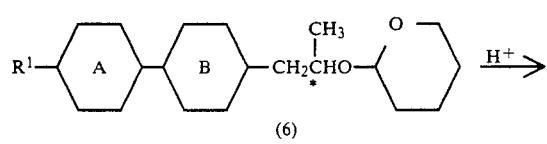
(6)

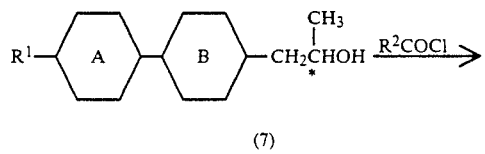
(7)

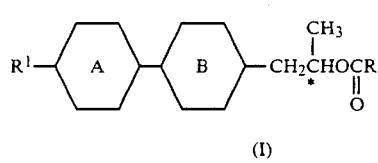
(I)

Namely, compound (4) is reacted with NaI to obtain 1-iodo-2-(2-tetrahydropyranyloxy)-propane (5) which is then converted into a Grignard reagent, followed by coupling to obtain a compound (6) which is subjected to removal of the protecting group (hereinafter referred to as "deprotection") to obtain an ω-substituted-2-alkanol (7) which is esterified to obtain the objective compound of the formula (I).

(b) When m = 0 and n = 2,

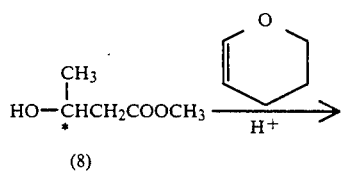
(8)

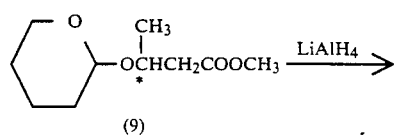
(9)

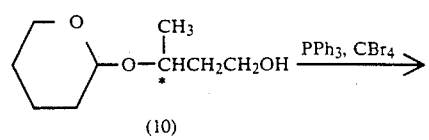
(10)

-continued

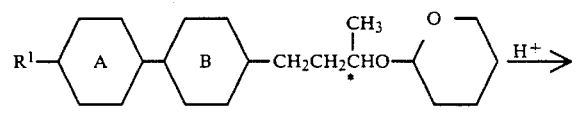
(11)

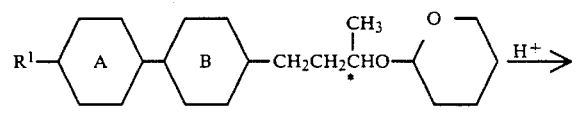

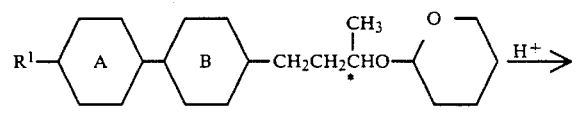
(12)

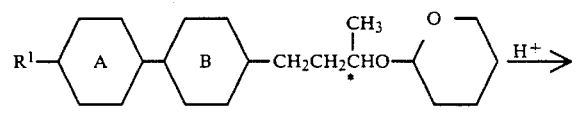
(13)

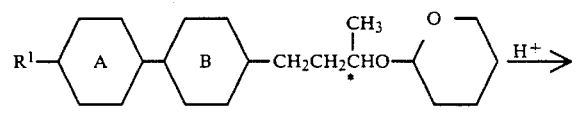
(I)

Namely, dihydropyran is reacted with methyl 3-hydroxy-butanoate (8) to obtain a tetrahydropyranyl compound (9) with which a reducing agent such as lithium aluminum hydride is reacted to obtain an alcohol (10) which is subjected to Br-substitution to obtain 1-bromo-3-(2-tetrahydropyranyloxy)-butane (11), which is converted into a Grinard reagent, followed by coupling to obtain a compound (12) which is subjected to deprotection to obtain an ω-substituted-2-alkanol (13) which is esterified to obtain the objective compound (I).

(c) When m = 0 and n ≧ 3,

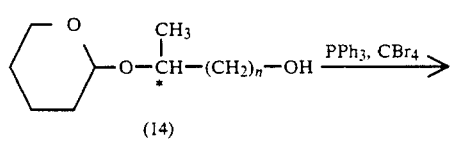
(14)

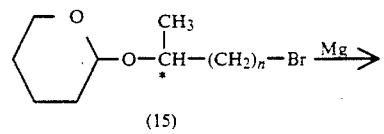
(15)

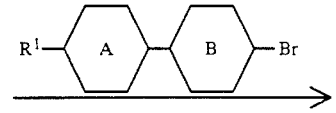

-continued

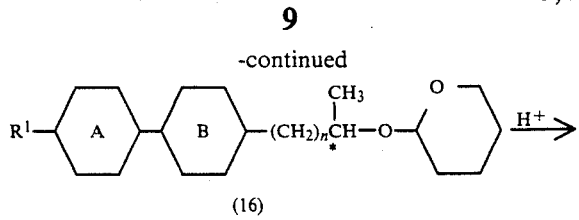

(16)

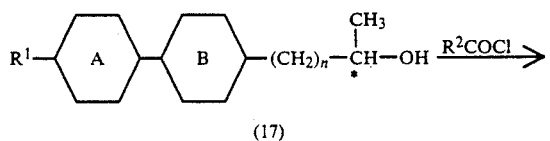

(17)

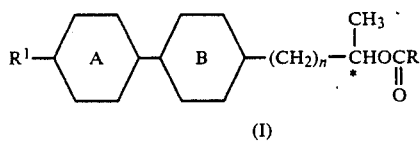

(I)

Namely, an alcohol (14) is brominated into a compound (15) which is subjected to coupling reaction to obtain a compound (16) which is deprotected and then esterified to obtain the objective compound (I).

4'-pentyl-4-(2'-(3''-methyl-pentanoyloxy)-propoxy)-biphenyl
4'-heptyl-4-(2'-pentanoyloxypropoxy)-biphenyl (S form, m.p. 59.1°-60.3° C.)
4'-heptyl-4-(2'-hexanoyloxypropoxy)-biphenyl (S form, m.p. 66.6°-68.6° C.)
4'-heptyl-4-(2'-octanoyloxypropoxy)-biphenyl (S form, m.p. 56.6°-57.3° C.)
4'-heptyl-4-(2'-(5''-methyl-heptanoyloxy)-propoxy)-biphenyl (2'S, 5'', m.p. 57.5°-60.6° C.)
4'-octyl-4-(2'-propanoyloxypropoxy)-biphenyl (S form, m.p. 44.4° C.)
4'-octyl-4-(2'-butanoyloxypropoxy)-biphenyl (S form, m.p. 50.7°-50.8° C.)
4'-octyl-4-(2'-pentanoyloxypropoxy)-biphenyl
4'-octyl-4-(2'-hexanoyloxypropoxy)-biphenyl (S form, m.p. 59.5°-60.1° C.)
4'-octyl-4-(2'-heptanoyloxypropoxy)-biphenyl (S form, m.p. 50.7° C.)
4'-octyl-4-(2'-octanoyloxypropoxy)-biphenyl
4'-hexyloxy-4-(2'-butanoyloxypropoxy)-biphenyl (S form, m.p. 74.4°-75.4° C.)
4'-hexyloxy-4-(2'-hexanoyloxypropoxy)-biphenyl (S form, m.p. 75.1°-76.0° C.)

(d) When m = 1,  Compound (4) (n = 1)
                 Compound (11) (n = 2)
                 Compound (15) (n ≧ 3)

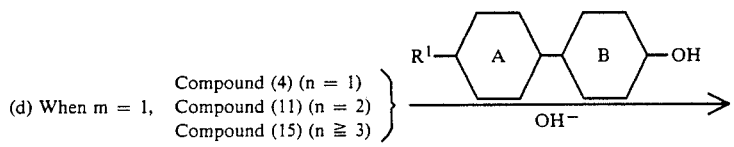

(18)

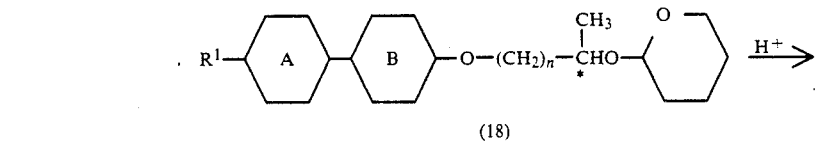

(19)

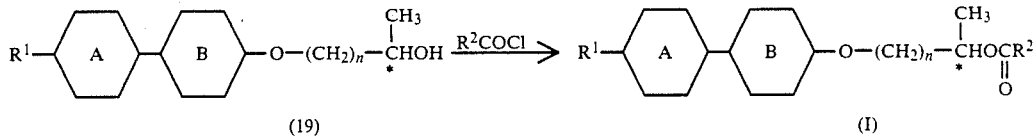

(I)

Namely, the respective raw materials, i.e. compound (4) in the case of n=1, compound (11) in the case of n=2 or compound (15) in the case of n≧3 are reacted with a phenol for etherification to obtain the corresponding compounds (18) which are deprotected to obtain the corresponding ω-substituted-2-alkanols (19) which are esterified to obtain the objective compounds (I).

Concrete representative examples of compounds of the formula (I) of the present invention obtained as above are as follows:
4'-pentyl-4-(2'-acetoxypropoxy)-biphenyl
4'-pentyl-4-(2'-propanoyloxypropoxy)-biphenyl
4'-pentyl-4-(2'-butanoyloxypropoxy)-biphenyl (S form, m.p. 50.8°-51.8° C.)
4'-pentyl-4-(2'-pentanoyloxypropoxy)-biphenyl (S form, m.p. 54.9°-55.9° C.)
4'-pentyl-4-(2'-hexanoyloxypropoxy)-biphenyl (S form, m.p. 53.8°-59.8° C.)
4'-pentyl-4-(2'-heptanoyloxypropoxy)-biphenyl (S form, m.p. 52.4°-53.0° C.)
4'-pentyl-4-(2'-octanoyloxypropoxy)-biphenyl
4'-pentyl-4-(2'-nonanoyloxypropoxy)-biphenyl 4'-hexyloxy-4-(2'-heptanoyloxypropoxy)-biphenyl (S form, m.p. 75.5°-76.8° C.)
4'-hexyloxy-4-(2'-nonanoyloxypropoxy)-biphenyl (S form, 79.2°-79.5° C.)
4'-hexyloxy-4-(2'-(4''-methylpentanoyloxy)-propoxy)-biphenyl
4'-hexyloxy-4-(2'-(4''-methylhexanoyloxy)-propoxy)-biphenyl (2'S, 4''S, m.p. 59.8°-60.9° C.)
4'-octyloxy-4-(2'-acetoxypropoxy)-biphenyl (S form, m.p. 81° C.)
4'-octyloxy-4-(2'-propanoyloxypropoxy)-biphenyl (S form, m.p. 77.1° C.)
4'-octyloxy-4-(2'-butanoyloxypropoxy)-biphenyl (S form, m.p. 70.9° C.)
4-octyloxy-4-(2'-pentanoyloxypropoxy)-biphenyl (S form, m.p. 76.3°-76.6° C.)
4'-octyloxy-4-(2'-hexanoyloxypropoxy)-biphenyl (S form, m.p. 74.5° C.)
4'-octyloxy-4-(2'-heptanoyloxypropoxy)-biphenyl (S form, m.p. 78°-78.4° C.)
4'-octyloxy-4-(2'-octanoyloxypropoxy)-biphenyl (S form, m.p. 78.8°-79.3° C.)
4'-octyloxy-4-(2'-nonanoyloxypropoxy)-biphenyl 4'-octyloxy-4-(2'-(2''-methylbutanoyloxy)-propoxy)-biphenyl (2'S, 2''S, m.p. 49° C.)
4'-octyloxy-4-(2'-(4''-methylhexanoyloxy)-propoxy)-biphenyl (2'S, 4''S, m.p. 56° C.)
4'-octyloxy-4-(2'-(3''-methylbutanoyloxy)-propoxy)-biphenyl (S form, m.p. 75° C.)
4'-octyloxy-4-(2'-(4''-methylpentanoyloxy)-propoxy)-biphenyl (S form, m.p. 77° C.)
4'-undecyloxy-4-(2'-propanoyloxypropoxy)-biphenyl (S form, m.p. 85.8°–86.3° C.)
4'-undecyloxy-4-(2'-pentanoyloxypropoxy)-biphenyl (S form, m.p. 82.7°–83.9° C.)
4'-undecyloxy-4-(2'-hexanoyloxypropoxy)-biphenyl
4'-undecyloxy-4-(2'-heptanoyloxypropoxy)-biphenyl (S form, m.p. 82.6°–83.7° C.)
4'-undecyloxy-4-(2'-octanoyloxypropoxy)-biphenyl (S form, m.p. 82.7°–83.9° C.)
4'-undecyloxy-4-(2'-(3''-methylbutanoyloxy)-propoxy)-biphenyl (S form, m.p. 80.9°–81.4° C.)
4'-undecyloxy-4-(2'-(5''-methylheptanoyloxy)-propoxy)-biphenyl (2'S, 5''S, m.p. 65.4°–66.5° C.)
4'-pentyl-3-fluoro-4-(2'-propanoyloxypropoxy)-biphenyl
4'-pentyl-3-fluoro-4-(2'-pentanoyloxypropoxy)-biphenyl
4'-pentyl-3-fluoro-4-(2'-hexanoyloxypropoxy)-biphenyl
4'-pentyl-3-fluoro-4-(2'-heptanoyloxypropoxy)-biphenyl
3'-fluoro-4'-octyloxy-4-(2'-butanoyloxypropoxy)-biphenyl
3'-fluoro-4'-octyloxy-4-(2'-pentanoyloxypropoxy)-biphenyl
3'-fluoro-4'-octyloxy-4-(2'-hexanoyloxypropoxy)-biphenyl
3'-fluoro-4'-octyloxy-4-(2'-(5''-methylheptanoyloxy)-propoxy)-biphenyl
4'-nonanoyl-3-fluoro-4-(2'-butanoyloxypropoxy)-biphenyl
4'-nonanoyl-3-fluoro-4-(2'-pentanoyloxypropoxy)-biphenyl
4'-nonanoyl-3-fluoro-4-(2'-hexanoyloxypropoxy)-biphenyl (S form, m.p. 79.7°–80.2° C.)
4'-nonanoyl-3-fluoro-4-(2'-(4''-methylhexanoyloxy)-propoxy)-biphenyl
4'-dodecanoyl-3-chloro-4-(2'-butanoyloxypropoxy)-biphenyl
4'-dodecanoyl-3-chloro-4-(2'-pentanoyloxypropoxy)-biphenyl
4'-dodecanoyl-3-chloro-4-(2'-heptanoyloxypropoxy)-biphenyl (S form, 43.7°–43.9° C.)
4'-dodecanoyl-3-chloro-4-(2'-(4''-methylhexanoyloxy)-propoxy)-biphenyl (2'S, 4''S, m.p. 43.2°–43.4° C.)
5-octyl-2-(4'-(2''-butanoyloxypropoxy)-phenyl)-pyrimidine (S form, m.p. 55° C.)
5-octyl-2-(4'-(2''-pentanoyloxypropoxy)-phenyl)-pyrimidine (S form, m.p. 61° C.)
5-octyl-2-(4'-(2''-heptanoyloxypropoxy)-phenyl)-pyrimidine (S form, m.p. 59° C.)
2-(4'-octylphenyl)-5-(2'-butanoyloxypropoxy)-pyrimidine (S form, m.p. 34.5°–35.9° C.)
2-(4'-octylphenyl)-5-(2'-pentanoyloxypropoxy)-pyrimidine (S form, m.p. 32.8°–33.3° C.)
2-(4'-octylphenyl)-5-(2'-hexanoyloxypropoxy)-pyrimidine (S form, m.p. 36.7°–38.4° C.)
2-(4'-octylphenyl)-5-(2'-heptanoyloxypropoxy)-pyrimidine (S form, m.p. 38.1°–39° C.)
2-(4'-octylphenyl)-5-(2'-(4''-methylhexanoyloxy)-propoxy)pyrimidine (2'S, 4''S, m.p. 33°–34.3° C.)
2-(4'-octylphenyl)-5-(2'-(3''-methylbutanoyloxy)-propoxy)pyrimidine (S form, m.p. 42.5°–42.7° C.)
5-octyl-2-(3'-fluoro-4'-(2''-pentanoyloxypropoxy)-phenyl)pyrimidine (S form, m.p. 34.1° C.)
5-octyloxy-2-(4'-(2''-butanoyloxypropoxy)-phenyl)-pyridine
5-octyloxy-2-(4'-(2''-pentanoyloxypropoxy)-phenyl)-pyrimidine
5-octyloxy-2-(4'-(2''-octanoyloxypropoxy)-phenyl)-pyrimidine
5-nonyl-2-(4'-(2''-butanoyloxypropoxy)-phenyl)-pyridine (S form, m.p. 46.5° C.)
5-nonyl-2-(4'-(2''-pentanoyloxypropoxy)-phenyl)-pyridine (S form, m.p. 45.2° C.)
5-nonyl-2-(4'-(2''-heptanoyloxypropoxy)-phenyl)-pyridine (S form, m.p. 48.7° C.)
5-octyl-2-(3'-fluoro-4'-(2''-pentanoyloxypropoxy)-phenyl)pyridine
3-(4'-octyloxyphenyl)-6-(2'-butanoyloxypropoxy)-pyridazine (S form, m.p. 72.7°–73.1° C.)
3-(4'-octyloxyphenyl)-6-(2'-pentanoyloxypropoxy)-pyridazine (S form, m.p. 67.2°–68.1° C.)
3-(4'-octyloxyphenyl)-6-(2'-heptanoyloxypropoxy)-pyridazine (S form, m.p. 56.5°–56.7° C.)
3-(4'-nonylphenyl)-6-(2'-propanoyloxypropoxy)-pyridazine (S form, m.p. 81.5°–82.6° C.)
3-(4'-nonylphenyl)-6-(2'-pentanoyloxypropoxy)-pyridazine (S form, m.p. 87.0° C.)
3-(4'-nonylphenyl)-6-(2'-hexanoyloxypropoxy)-pyridazine (S form, m.p. 90.2°–92.0° C.)
2-(4'-octyloxyphenyl)-5-(2'-butanoyloxypropoxy)-pyrazine
2-(4'-octyloxyphenyl)-5-(2'-pentanoyloxypropoxy)-pyrazine
2-(4'-octyloxyphenyl)-5-(2'-heptanoyloxypropoxy)-pyrazine
1-(4'-pentyl-trans-cyclohexyl)-4-(2'-butanoyloxypropoxy)benzene (S form, m.p. 28.4° C.)
1-(4'-pentyl-trans-cyclohexyl)-4-(2'-pentanoyloxypropoxy)benzene
1-(4'-pentyl-trans-cyclohexyl)-4-(2'-hexanoyloxypropoxy)benzene (S form, m.p. 21.4° C.)
4'-heptyl-4-(2'-(2''-ethoxyacetoxy)-propoxy)-biphenyl (S form, m.p. 59.9°–60.3° C.)
4'-octyl-4-(2'-(2''-methoxyacetoxy)-propoxy)-biphenyl
4'-octyloxy-4-(2'-(2''-ethoxyacetoxy)-propoxy)-biphenyl (S form, m.p. 84.6°–85° C.)
4'-octyloxy-4-(2'-(3''-ethoxypropanoyloxy)-propoxy)-biphenyl (S form, m.p. 57.5°–57.7° C.)
5-nonyl-2-(4'-(2''-(3''-ethoxypropanoyloxy)-propoxy)-phenyl)pyridine (S form, m.p. 40°–40.4° C.)
5-nonyl-2-(4'-(2''-(2''-ethoxyacetoxy)-propoxy)-phenyl)pyridine (S form, m.p. 47.7°–48.6° C.)
5-octyl-2-(4'-(2''-(2''-methoxyacetoxy)-propoxy)-phenyl)pyrimidine (S form, m.p. 45.6°–47° C.)
5-octyloxy-2-(4'-(2''-(3''-methoxypropanoyloxy)-propoxy)phenyl)-pyrimidine
2-(4'-octylphenyl)-5-(2'-(2''-ethoxyacetoxy)-propoxy)-pyrimidine (S form, m.p. 47.7°–48.6° C.)
2-(4'-heptyloxyphenyl)-5-(2'-(3''-methoxypropanoyloxy)propoxy)-pyrimidine
1-(4'-pentyl-trans-cyclohexyl)-4-(2'-(2''-ethoxyacetoxy)propoxy)-benzene
3-(4'-octyloxyphenyl)-6-(2'-(3''-ethoxypropanoyloxy)-pyridazine (S form, m.p. 58.5°–59° C.)
2-(4'-octyloxyphenyl)-5-(2'-(2''-methoxyacetoxy)-propoxy)pyradine 4-butyl-4-(2'-(4'''-keto-pentanoyloxy)-propoxy)-biphenyl 4'-hexyl-4-(2'-(5''-keto-hexanoyloxy)-propoxy)-biphenyl 4'-nonyl-4-(2'-(5''-keto-heptanoyloxy)-propoxy)-biphenyl 4'-octyloxy-4-(2'-(4''-keto-pentanoyloxy)-propoxy)-biphenyl (S form, m.p. 80.5° C.)

4'-octyloxy-4-(2'-(5''-keto-hexanoyloxy)-propoxy)-biphenyl (S form, m.p. 89.1° C.)

5-octyl-2-(4'-(2''-(4'''-keto-pentanoyloxy)-propoxy)-phenyl)pyridine 5-nonyl-2-(4'-(2''-(4'''-keto-pentanoyloxy)-propoxy)-phenyl)pyridine (S form, m.p. 49.3° C.)

5-nonyl-2-(4'-(2''-(5'''-keto-hexanoyloxy)-propoxy)-phenyl)pyridine 5-octyl-2-(4'-(2''-(4'''-keto-pentanoyloxy)-propoxy)-phenyl)pyrimidine 5-octyloxy-2-(4'-(2''-(5'''-keto-hexanoyloxy)-propoxy)-phenyl)-pyrimidine 2-(4'-octylphenyl)-5-(2'-(4''-keto-pentanoyloxy)-propoxy)pyrimidine 2-(4'-heptyloxyphenyl)-5-(2'-(5''-keto-hexanoyloxy)-propoxy)-pyrimidine 1-(4'-pentyl-trans-cyclohexyl)-4-(2'-(4''-keto-pentanoyloxy)-propoxy)-benzene 3-(4'-octyloxyphenyl)-6-(2'-(5''-keto-hexanoyloxy)-propoxy)-pyridazine 2-(4'-octyloxyphenyl)-5-(2'-(4''-k-to-pentanoyloxy)-propoxy)-pyridine 4'-octyloxy-4-(3'-butanoyloxybutoxy)-biphenyl (S form, m.p. 57.4°–57.7° C.)

4'-octyloxy-4-(3'-pentanoyloxybutoxy)-biphenyl (R form, m.p. 50° C.)

4'-octyloxy-4-(3'-heptanoyloxybutoxy)-biphenyl (R form, m.p. 56.4°–56.8° C.)

2-(4'-octylphenyl)-5-(3'-pentanoyloxybutoxy)-pyrimidine (R form, oily at room temperature)

2-(4'-octylphenyl)-5-(3'-hexanoyloxybutoxy)-pyrimidine (R form, oily at room temperature)

5-octyl-2-(4'-(3''-propanoyloxybutoxy)-phenyl)-pyrimidine 5-octyl-2-(4'-(3''-heptanoyloxybutoxy)-phenyl)-pyrimidine 5-octyloxy-2-(4'-(3''-butanoyloxybutoxy)-phenyl)-pyrimidine 5-octyloxy-2-(4'-(3''-hexanoyloxybutoxy)-phenyl)-pyrimidine 5-octyl-2-(4'-(3''-butanoyloxybutoxy)-phenyl)-pyridine (R form, m.p. 44.7°–45.6° C.)

5-octyl-2-(4'-(3''-pentanoyloxybutoxy)-phenyl)-pyridine (R form, m.p. 46.5°–47.5° C.)

5-octyl-2-(4'-(3''-hexanoyloxybutoxy)-phenyl)-pyridine (R form, m.p. 49.9°–50.4° C.)

1-(4'-pentyl-trans-cyclohexyl)-4-(3''-pentanoyloxybutoxy)benzene 3-(4'-octylphenyl)-6-(3'-hexanoylbutoxy)-pyridazine 2-(4'-octyloxyphenyl)-5-(3'-butanoyloxybutoxy)-pyrazine 4'-octyloxy-4-(4'-butanoyloxypentoxy)-biphenyl 2-(4'-octylphenyl)-5-(4'-hexanoylpentoxy)-pyrimidine 5-octyl-2-(4'-(4''-pentanoyloxypentoxy)-phenyl)-pyrimidine 5-octyloxy-2-(4'-(4''-heptanoyloxypentoxy)-phenyl)-pyrimidine 5-octyl-2-(4'-(4''-butanoyloxypentoxy)-phenyl)-pyrimidine 1-(4'-hexyl-trans-cyclohexyl)-4-(4'-hetanoyloxypentoxy)benzene 3-(4'-octyloxyphenyl)-6-(3'-propanoyloxypentoxy)-pyridazine 2-(4'-octylphenyl)-5-(3'-octanoyloxpentoxy)-pyrazine 4'-heptyl-4-(5'-propanoyloxyhexyloxy)-biphenyl 2-(4'-octyloxyphenyl)-5-(6'-butanoyloxyheptyloxy)-pyrimidine 5-octyl-2-(4'-(7''-hexanoyloxyoctyloxy)-phenyl)-pyridine 1-(4'-octyl-trans-cyclohexyl)-4-(8'-heptanoyloxynonyloxy)benzene -butanoyloxydecyloxy)-pyridazine 2-(4'-octyloxyphenyl)-5-(10'-propanoyloxyundecyloxy)-pyrazine The compounds and liquid crystal compositions of the first aspect of the present invention will be described below in more detail by way of examples, it being understood that this aspect of the invention is not limited to these examples. All percents are by weight unless otherwise indicated.

EXAMPLE 1

Preparation of S-4'-octyloxy-4-(2'-pentanoyloxypropoxy)-biphenyl (a compound of the formula (I) wherein $R^1$ represents $C_8H_{17}O$; $R^2$ represents $C_4H_9$;

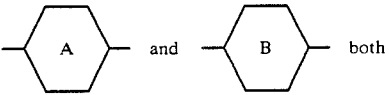 and 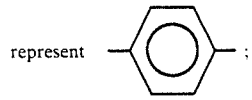 both represent m represents 1; and n represents 1)

A mixture of (2S)-2-tetrahydropyranyloxy-1-hydroxypropane (137 g, 0.85 mol) prepared according to the method described in the literature (C. Malanga et al., Synthetic Communications, 12 (1), 67–70 (1982)), with anhydrous pyridine (600 g) was cooled with ice, followed by dropwise adding to the mixture a solution of p-toluenesulfonyl chloride (165 g, 0.87 mol) dissolved in pyridine (200 ml), agitating the mixture at 0° C. for 2 hours, successively agitating it at room temperature for 2 hours, allowing it to stand overnight, adding toluene (1 l), further adding 2N-NaOH aqueous solution (500 ml), separating the resulting organic layer, washing it several times with water to make it neutral, drying with MgSO4 and distilling off the solvent to obtain (2S)-2-(2'-tetrahydropyranyloxy)-1-(p-toluenesulfonyloxy)-propane (257 g, yield 95.9%). A solution of this product (20 g) dissolved in N,N-dimethylformamide (hereinafter abbreviated to DMF) (300 ml) was added to a mixture of sodium hydride (60%, 2 g), 4-hydroxy-4'-octyloxybiphenyl (10 g) and tetrahydrofuran (hereinafter abbreviated to THF) (200 ml), followed by agitating the mixture at 60° C. for 4 hours, allowing it to cool down to room temperature, adding toluene (300 ml) and water (300 ml), separating the resulting organic layer, washing it with an alkali, washing with water, concentrating, adding ethanol (300 ml) and pyridium p-toluenesulfonate (hereinafter abbreviated to PPTS) (2 g), agitating the mixture at 50° C. for 3 hours, distilling off ethanol, adding toluene (300 ml), washing the resulting organic layer with water, concentrating it and recrystallizing to obtain S-1-(4'-octyloxy-4-biphenylyloxy)propan-2-ol (8 g). A mixture of this product (1.5 g), pentanoylchloride (0.8 g) and pyridine (50 ml) was heated to 60° C. for 2 hours. After the reaction, the resulting material was purified to obtain the objective S-4'-octyloxy-4-(2'-pentanoyloxypropoxy)-biphenyl (0.8 g). m.p.: 76.3°-76.6° C.

EXAMPLE 2

Preparation of S-4'-octyloxy-4-(2'-butoxycarbonyloxypropoxy)-biphenyl (a compound of the formula (I) wherein $R^1$ represents $C_8H_{17}O$, $R^2$ represents $C_4H_9O$,

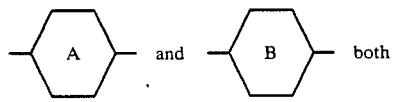

represent 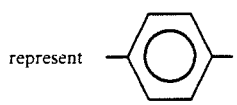, m represents 1 and n represents 1)

A mixture of S-1-(4'-octyloxy-4-biphenylyloxy)-propan-2-ol (1.5 g) obtained as an intermediate in the steps of Example 1, butyl chloroformate (0.9 g) and pyridine (10 ml) was reacted in the same manner as in Example 1, followed by purification to obtain S-4'-octyloxy-4-(2'-butoxycarbonyloxypropoxy)-biphenyl (0.7 g). m.p.: 66.9°-6458

EXAMPLE 3

Preparation of S-4'-octyloxy-4-(2'-heptanoyloxypropoxy)-biphenyl (a compound of the formula (I) wherein $R^1$ represents $C_8H_{17}O$; $R^2$ represents $C_6H_{13}$;

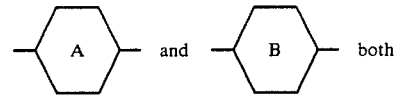

represent 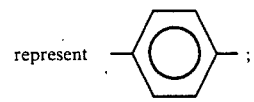;

m represents 1; and n represents 1)

S-1-(4'-octyloxy-4-biphenylyloxy)-propan-2-ol (1.5 g) obtained as an intermediate in the preparation of Example 1, heptanoic acid (0.5 g), N,N-dicyclohexylcarbodiimide (hereinafter abbreviated to DCC) (1.3 g) and 4-N,N-dimethylaminopyridine (hereinafter abbreviated to DMAP) (0.1 g) were agitated in dichloromethane (50 ml) at room temperature for 4 hours, followed by filtering off the resulting solids and purifying the mother liquor to obtain the captioned compound (m.p. 78.0°-78.4° C.).

EXAMPLE 4

Preparation of (2'S, 2''S)-4'-octyloxy-4-(2'-(2''-methylbutylyloxy)-propoxy)-biphenyl (a compound of the formula (I) wherein $R^1$ represents $C_8H_{17}O$; $R^2$ represents

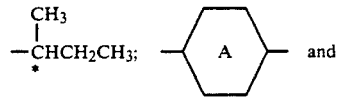

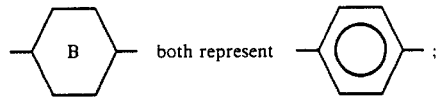

m represents 1; and n represents 1)

Example 3 was repeated except that heptanoic acid in Example 3 was replaced by S-2-methylbutanoic acid, to obtain the captioned compound (m.p. 49° C.).

EXAMPLE 5 (COMPOSITION 1)

A liquid crystal composition A consisting of

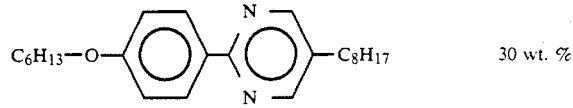 30 wt. %

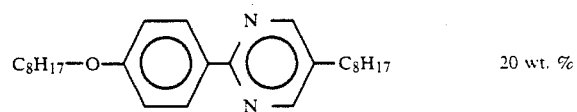 20 wt. %

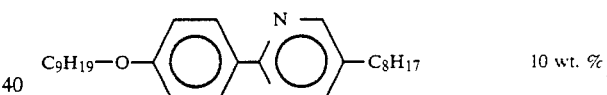 10 wt. %

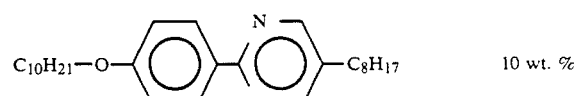 10 wt. %

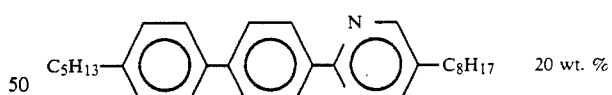 20 wt. % and

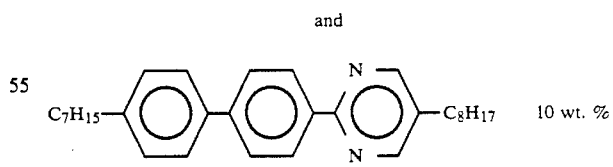 10 wt. % exhibits the following phase transition points:
C→SC:4° C., SC→SA: 65° C., SA→N: 79° C. and N→I: 90° C.
wherein C, SA, N and I are abbreviations of crystalline phase, smectic A phase, nematic phase and isotropic liquid, respectively. Further, since this composition consists only of non-optically active compounds, it is not a chiral liquid crystal and hence exhibits no spontaneous polarization.

A composition B consisting of 80% by weight of the above composition A and 20% by weight of the compound of Example 1 of the present invention exhibits the following phase transition points:
SC*→SA: 46° C., SA→Ch: 73.8° C. and Ch→I: 80.2° C.,
although the phase transition point of C→SC* is unclear.

This composition B was sealed in a cell of 2 μm thickness provided with transparent electrodes obtained by applying PVA (polyvinyl alcohol) as an aligning agent onto the surface and rubbing the resulting surface to subject it to parallel aligning treatment, followed by providing the resulting element between two crossed polarizers and impressing an electric field thereto. As a result, change in the intensity of transmitted light was observed by impressing ±10 V. Response time was sought from the change in the intensity of transmitted light at that time and the spontaneous polarization value Ps was sought according to Sowyer-Tower method. The results were as follows:

| Temperature (°C.) | Response time (μsec) | Ps (nC/cm$^3$) |
|---|---|---|
| 40 | 18 | 5.7 |
| 35 | 28 | 8.5 |
| 30 | 36 | 10.1 |
| 25 | 48 | 11.3 |

As shown above, when the compound of the formula (I) of the present invention was used, it was possible to impart Ps to an achiral smectic composition and a ferroelectric liquid crystal composition exhibiting a response time of about 50 μsec at room temperature was obtained.

EXAMPLE 6 (Composition 2)

A liquid crystal composition C consisting of

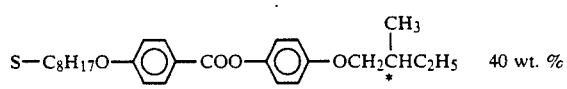 40 wt. %

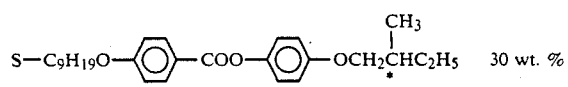 30 wt. % and

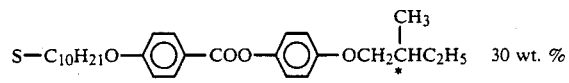 30 wt. % exhibits the following phase transition points:
C→SB: 17° C., SB→SC*: 22° C., SC*→SA: 45° C. and SA→I: 59° C.

A liquid crystal composition D obtained by adding 20% by weight of the compound of Example 1 of the present invention to 80% by weight of the composition C exhibited the following phase transition points:
SC*→SA: 36° C. and SA→I: 53° C.
although the phase transition point of C→SC* was unclear.

The response times and Ps values of the compositions C and D were measured under the same conditions as in Example 5 (Composition 1). The results were as follows:

| Composition | Temperature (°C.) | Response time (μsec) | Ps (nC/cm$^3$) |
|---|---|---|---|
| C | 25 | 2300 | 4.0 |
| D | 30 | 81 | 26.4 |
| D | 25 | 125 | 35.9 |
| D | 20 | 196 | 42.5 |

As shown above, when the compound of the formula (I) of the present invention is added to a composition which is a chiral smectic liquid crystal composition, but has a small Ps value and a low response rate, it is possible to increase the Ps value of the composition and reduce the response time down to a value as small as about 1/20.

EXAMPLE 7 (Composition 3)

A mixture (liquid crystal composition E) consisting of 90% by weight of the liquid crystal composition A used in Example 5 (Composition 1) and 10% by weight of S-5-nonyl-2-(4'-(2''-butanoyloxypropoxy)-phenyl)-pyridine (m.p. 46.5° C.) (a compound of the present invention) exhibits the following phase transition points:
SC*→SA, 46.5° C.; SA→Ch, 73.8° C.; and Ch→I, 82.5° C.

The response time and Ps of the liquid crystal composition E were measured under the same conditions as in Example 5 (Composition 1). The results are as follows:

| Temperature (°C.) | Response time (μsec) | Ps (nC/cm$^2$) |
|---|---|---|
| 40 | 50 | 3.3 |
| 30 | 85 | 4.3 |
| 20 | 110 | 4.7 |

As shown above, when 10% by weight of the compound of the present invention is used, the resulting composition has a sufficiently short response time.

EXAMPLE 8 (Composition 4)

A nematic liquid crystal composition consisting of

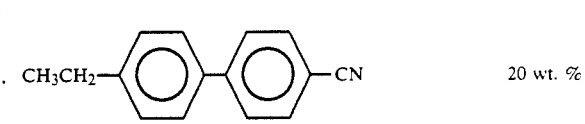 20 wt. %

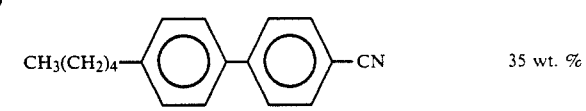 35 wt. %

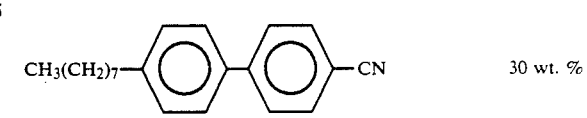 30 wt. % and

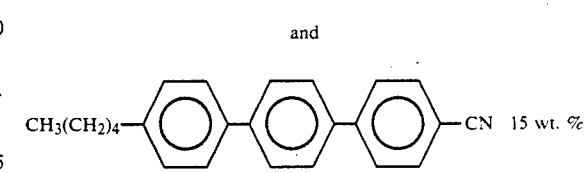 15 wt. % was filled in a cell provided with transparent electrodes obtained by applying polyvinyl alcohol (PVA) as an aligning agent onto the surfaces thereof and rubbing the resulting surfaces to subject them to parallel aligning treatment and having a distance between the electrodes of 10 μm to prepare a TN display cell, which was observed under a polarizing microscope. As a result, formation of a reverse twist domain was observed.

To this nematic liquid crystal composition was added (S)-5-octyl-2-(4'-(2''-butanoyloxypropoxy)-phenyl)-pyrimidine in an amount of 0.5% by weight, and the resulting TN type cell was observed in the same manner as above. As a result no reverse twist domain formed, but a uniform nematic phase was observed.

EXAMPLE 9 (Composition 5)

(S)-3-(4'-nonylphenyl)-6-(2'-pentanoyloxypropoxy)-pyridazine as a compound of the present invention in an amount of 1% by weight was added to a commercially available nematic liquid crystal composition (ZLI-1132, tradename of a product of Merck Co., Ltd.) to obtain a chiral nematic liquid crystal composition the chiral pitch of which was then measured according to Cano wedge method (Applied Physics 43 (2), 126–131 (1974)). The composition exhibited the following negative temperature characteristics:

| Temperature | Pitch (μm) |
|---|---|
| 20 | 15.2 |
| 30 | 14.7 |
| 40 | 14.3 |
| 50 | 14.1 |
| 60 | 14.1 |

SECOND ASPECT OF THE INVENTION

In formula (I'), $R^{1'}$ preferably represents an alkyl group having from 4 to 16 carbon atoms or an alkoxy group having from 4 to 16 carbon atoms.

$R^{2'}$ preferably represents an alkyl group, an alkanoyl group or an alkoxyalkanoyl group, and more preferably contains up to 10 carbon atoms. The group represented by $R^{2'}$ may be optically active or inactive.

A combination of the rings A and B preferably includes

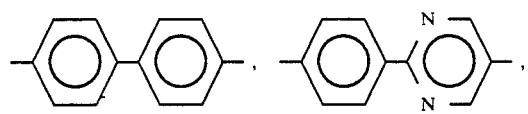

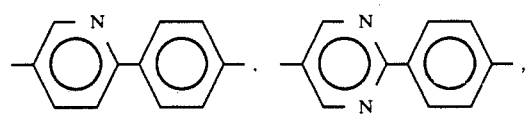

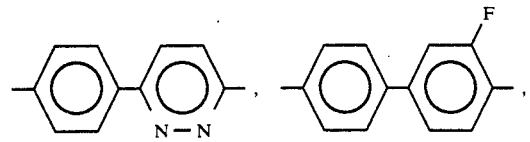

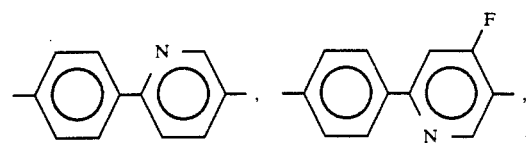

-continued

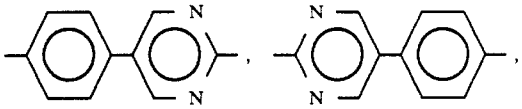

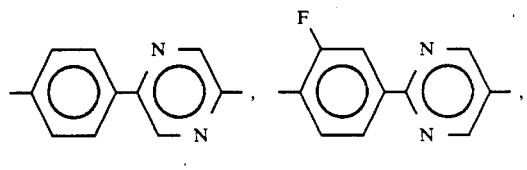

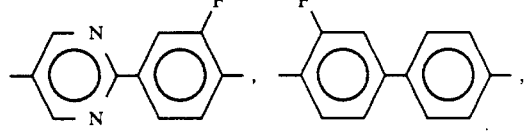

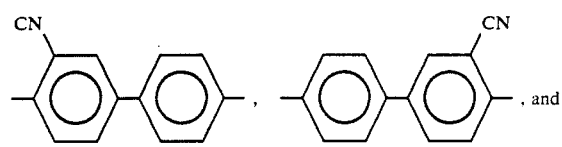

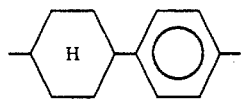

with the first six combinations being more preferred.

A sub-group of compounds within the scope of formula (I') are those represented by the formula (I''):

$$R^{1'}-A-B-O-CH_2\overset{*}{C}H(CH_3)CH_2-O-\overset{O}{\overset{\|}{C}}-R^{2''} \qquad (I'')$$

wherein $R^{1'}$ represents a straight chain alkyl or alkoxy group, each of 7 to 10 carbon atoms, $R^{2''}$ represents a straight chain alkyl group of 3 to 14 carbon atoms, an optically active alkyl group of 4 to 14 carbon atoms having a methyl branch, or an alkoxyalkyl group of 3 to 14 carbon atoms, —A—B— represents

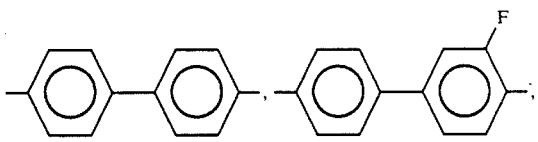

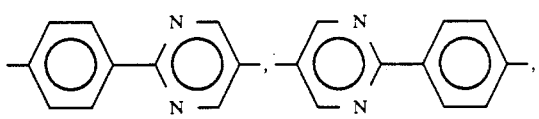

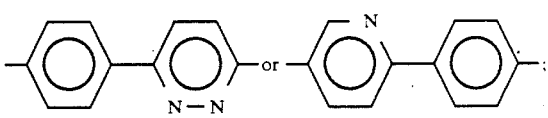

and the asterisk mark * indicates that the carbon atom provided with * is an asymmetrical carbon atom.

Typical examples of the compounds represented by formula (I') are shown in Table 1 below along with their melting points.

TABLE 1

| Compound No. | R¹' | —A—B— | R²' | Absolute Configuration | Melting Point (°C.) | Remark |
|---|---|---|---|---|---|---|
| 1 | n-C$_8$H$_{17}$O | 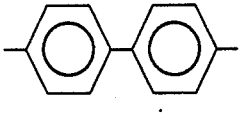 | $-\overset{O}{\underset{\|}{C}}-(CH_2)_2CH_3$ | S | 73.6–74.4 | Example 10 |
| 2 | n-C$_8$H$_{17}$O | 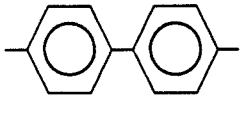 | $-\overset{O}{\underset{\|}{C}}-(CH_2)_4CH_3$ | S | 62.4 | |
| 3 | n-C$_8$H$_{17}$O | 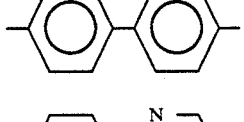 | $-\overset{O}{\underset{\|}{C}}-(CH_2)_2\overset{*}{C}H(CH_3)CH_2CH_3$ | S,S | 57.6 | |
| 4 | n-C$_7$H$_{15}$O | 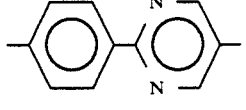 | $-\overset{O}{\underset{\|}{C}}-(CH_2)_3CH_3$ | R | 39.4 | |
| 5 | n-C$_7$H$_{15}$O | 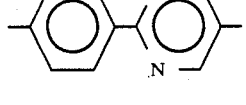 | $-\overset{O}{\underset{\|}{C}}-(CH_2)_5CH_3$ | R | 36.0 | |
| 6 | n-C$_7$H$_{15}$O | 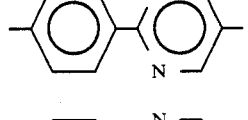 | $-\overset{O}{\underset{\|}{C}}-\overset{*}{C}H(CH_3)O(CH_2)_3CH_3$ | R,S | 20.0 | |
| 7 | n-C$_7$H$_{15}$O | 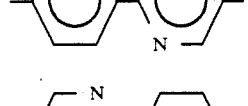 | $-(CH_2)_3CH_3$ | S | 22.2 | |
| 8 | n-C$_8$H$_{17}$ | 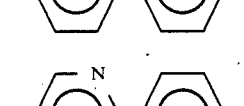 | $-\overset{O}{\underset{\|}{C}}-(CH_2)_2CH_3$ | R | 55.8 | |
| 9 | n-C$_8$H$_{17}$ | 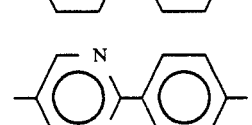 | $-\overset{O}{\underset{\|}{C}}-(CH_2)_4CH_3$ | R | 57.4 | |
| 10 | n-C$_8$H$_{17}$ | 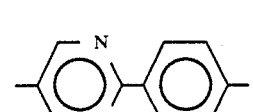 | $-\overset{O}{\underset{\|}{C}}-(CH_2)_2CH_3$ | R | 30.0 | |
| 11 | n-C$_8$H$_{17}$ | 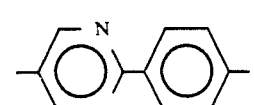 | $-\overset{O}{\underset{\|}{C}}-(CH_2)_3CH_3$ | R | 31.8 | |
| 12 | n-C$_8$H$_{17}$ | 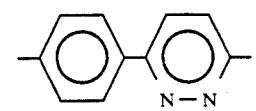 | $-\overset{O}{\underset{\|}{C}}-(CH_2)_3\overset{*}{C}H(CH_3)CH_2CH_3$ | R,S | 38.8 | |
| 13 | n-C$_8$H$_{17}$O |  | $-\overset{O}{\underset{\|}{C}}-(CH_2)_3CH_3$ | R | 59.4 | |

TABLE 1-continued

| Compound No. | R¹' | —A—B— | R²' | Absolute Configuration | Melting Point (°C.) | Remark |
|---|---|---|---|---|---|---|
| 14 | n-C$_8$H$_{17}$O | biphenyl with N—N | $-\overset{O}{\underset{\|\|}{C}}-\overset{*}{\underset{\|}{C}}\text{HO(CH}_2)_3\text{CH}_3$ with CH$_3$ | R,S | 51.9 | |
| 15 | n-C$_8$H$_{17}$O | biphenyl with N—N | $-\overset{O}{\underset{\|\|}{C}}-(\text{CH}_2)_3\overset{*}{\underset{\|}{C}}\text{HCH}_2\text{CH}_3$ with CH$_3$ | R,S | 53.5 | |
| 16 | n-C$_{12}$H$_{25}$ | biphenyl with F | $-\overset{O}{\underset{\|\|}{C}}-(\text{CH}_2)_3\text{CH}_3$ | R | 37.3 | |
| 17 | n-C$_{12}$H$_{25}$ | biphenyl with F | $-\overset{O}{\underset{\|\|}{C}}-(\text{CH}_2)_4\text{CH}_3$ | R | 36.4 | |

Although many of the compounds according to the second aspect of the present invention have no liquid crystal properties by themselves, they provide ferroelectric liquid crystal compositions having high Ps when combined with non-chiral smectic liquid crystal compounds or chiral smectic liquid crystal compounds. For example, a liquid crystal composition exhibiting a non-chiral smectic C phase which does not show spontaneous polarization becomes a ferroelectric liquid crystal composition on addition of 20% by weight of one of the compounds according to the present invention. The resulting composition has a high Ps and a short response time. Further, addition of the compound of the present invention to a ferroelectric liquid crystal composition having a small Ps and a long response time increases the Ps and reduces the response time. Thus, the compounds of the present invention are very suitable as a constituting component of ferroelectric liquid crystal composition.

The non-chiral smectic liquid crystal compounds to be used in combination with the compounds of formula (I') include 5-alkyl-2-(4'-alkoxyphenyl)pyrimidine compounds, e.g., 5-octyl-2-(4'-octyloxyphenyl)pyrimidine, 5-octyl-2-(4'-nonyloxyphenyl)pyrimidine, 5-octyl-2-(4'-decyloxyphenyl)pyrimidine, etc.; 5-alkyl-2-(4'-alkoxyphenyl)pyridine compounds, e.g., 5-heptyl-2-(4'-octyloxyphenyl)pyridine, 5-octyl-2-(4'-octyloxyphenyl)pyridine, 5-heptyl-2-(4'-nonyloxyphenyl)pyridine, 5-nonyl-2-(4'-nonyloxyphenyl)pyridine, etc.; 5-alkyl-2-(4'-alkyl-4-biphenylyl)pyrimidine 5-hexyl-2-(4'-octyl-4-biphenylyl)pyrimidine, etc.; 4-alkoxyphenyl-4-alkoxybenzoate compounds, e.g., 4-octyloxyphenyl 4-octyloxybenzoate, 4-nonyloxyphenyl 4-octyloxybenzoate, 4-decyloxyphenyl 4-nonyloxybenzoate, etc.; and the like.

The chiral smectic liquid crystal compounds to be used in combination with the compounds of formula (I') include optically active phenyl benzoate compounds, e.g., 4-(2'-methylbutyloxy)phenyl 4-octyloxybenzoate, 4-(6'-methyloctyloxy)phenyl 4-nonyloxybenzoate, etc.; optically active 5-alkylphenylpyrimidine compounds, e.g., 5-octyl-2-[4'-(6''-methyloctyloxy)phenyl]pyrimidine, 5-nonyl-2-[4'-(5''-methylheptyloxy)phenyl]pyrimidine, etc.; and optically active 5-alkylphenylpyridine compounds, e.g., 5-heptyl-2-[4'-(6''-methyloctyloxy)phenyl]pyridine, 5-octyl-2-[4'-(5''-methylheptyloxy)phenyl]pyridine, etc.

Since the compounds of formula (I') have an optically active carbon atom, they induce a twisted structure when added to a nematic liquid crystal. A nematic liquid crystal having the twisted structure, i.e., a chiral nematic liquid crystal, does not produce so-called reverse domains in a TN type liquid crystal display element so that the compounds of formula (I') can be used as an agents for preventing reverse domain formation.

The compounds of formula (I') can be synthesized through, for example, the following reaction route:

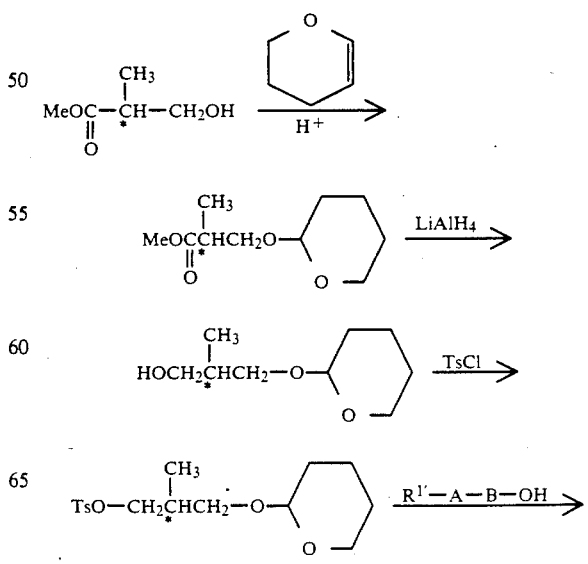

-continued

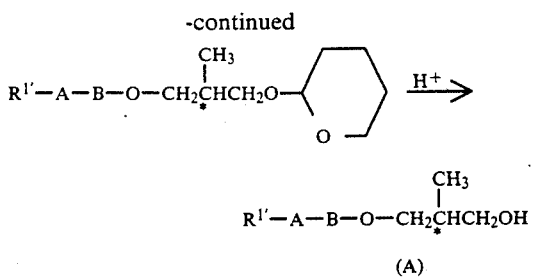
(A)

When R²' is an alkyl group, an alkoxyalkyl group or a halogenated alkyl group,

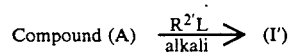

When R²' is an alkanoyl group, an alkoxyalkanoyl group or a halogenated alkanoyl group,

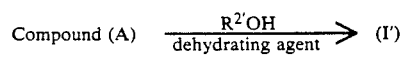

When R²' is an alkoxycarbonyl group,

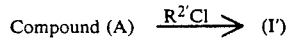

wherein R¹', R²', A, and B are as defined above; Ts represents a p-toluenesulfonyl group; and L represents a releasable group, such as a p-toluenesulfonyl group, a methanesulfonyl group, an iodine atom, and a bromine atom.

The second aspect of the present invention will now be illustrated in greater detail by way of the following Examples, but it should be understood that this aspect of the present invention is not limited thereto. In these Examples, all the percents are by weight unless otherwise indicated.

EXAMPLE 10

Preparation of S-4'-Octyloxy-4-(2-methyl-3-butanoyloxypropoxy)-biphenyl [the compound of formula (I') wherein R¹': an octyloxy group; R²': a butanoyl group; and —A—B—:

25 g of R-methyl 2-methyl-3-hydroxy-propionate, 21 g of 3,4-dihydropyran, 2 ml of concentrated hydrochloric acid, and 50 ml of anhydrous dichloromethane were mixed under ice-cooling, and the mixture was allowed to stand overnight. The mixture was washed with a 5% aqueous solution of sodium hydrogencarbonate and dried over magnesium sulfate. The solvent was removed by distillation, and the residue was distilled under reduced pressure to obtain 40 g of R-methyl 2-methyl-3-(2-tetrahydropyranyloxy)propionate having as boiling point of from 92° to 96° C./5 mmHg.

In 50 ml of tetrahydrofuran (THF) was suspended 7 g of lithium aluminum hydride, and 200 ml of a THF solution containing the whole quantity of the above prepared R-methyl 2-methyl-3-(2-tetrahydropyranyloxy)propionate was added to the suspension dropwise under cooling. After completion of the reaction, water and a 2N aqueous solution of sodium hydroxide were added to the reaction mixture, and any inorganic substance was separated by filtration. The filtrate was dried over magnesium sulfate, and the solvent was removed by distillation. The residue was distilled under reduced pressure to obtain 36 g of S-2-methyl-3-(2-tetrahydropyranyloxy)propan-1-ol having a boiling point of 68 to 75° C./1.5 mmHg.

In 500 ml of pyridine was dissolved 15 g of the resulting product, and 100 ml of a pyridine solution containing 16.4 g of p-toluenesulfonyl chloride was added dropwise thereto under ice-cooling, followed by allowing to stand overnight. The reaction mixture was extracted with 300 ml of toluene, and the extract was washed with water and dried over magnesium sulfate. The solvent was removed by distillation to obtain 25 g of R-1-(p-toluenesulfonyloxy)-2-methyl-3-(2-tetrahydropyranyloxy)propane.

In 150 ml of THF was suspended 2.0 g of sodium hydride (55% in oil), and 200 ml of a THF solution containing 10 g of 4'-octyloxy-4-hydroxy-biphenyl was added to the suspension under ice-cooling. To the mixture was further added 300 ml of a dimethylformamide solution of 15 g of the above prepared R-1-(p-toluenesulfonyloxy)-2-methyl-3-(2-tetrahydropyranyloxy)propane, and the resulting mixture was stirred at 60° C. for 5 hours. After allowing the mixture to cool, 500 ml of toluene was added thereto. The reaction mixture was washed successively with water and an alkali, and the solvent was removed by distillation. To the residue were added 300 ml of ethanol and 3 g of p-toluenesulfonic acid monohydrate, followed by heating at 50° C. for 1 hour. After allowing to cool, the crystals were allowed to grow under cooling. Filtration gave 11 g of R-4'-octyloxy-4-(2-methyl-3-hydroxypropoxy)biphenyl. A mixture of 1 g of this product, 0.4 g of butanoic acid, 1.0 g of N,N-dicyclohexylcarbodiimide, 0.1 g of 4-N,N-dimethylaminopyridine, and 30 ml of dichloromethane was stirred at room temperature for 6 hours. The formed solid was separated by filtration, and the filtrate was washed successively with an acid, an alkali, and water, dried over magnesium sulfate, and distilled to remove the solvent. The residue was purified by chromatography using a column packed with active alumina. Recrystallization from ethanol yielded 0.7 g of S-4'-octyloxy-4-(2-methyl-3-butanoyloxy-propoxy)-biphenyl having a melting point of from 73.6° to 74.4° C.

EXAMPLE 11 (COMPOSITION 6)

Liquid Crystal Composition A having the following formulation was prepared.

Formulation:

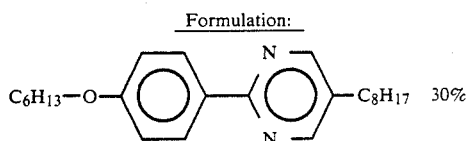 30%

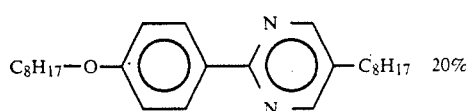 20%

-continued
Formulation:

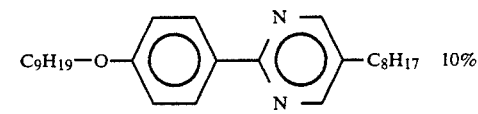 10%

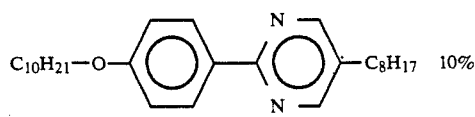 10%

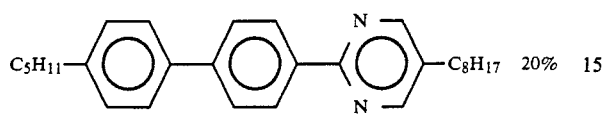 20%

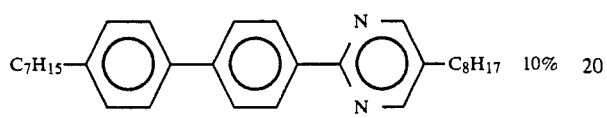 10%

Composition A was a non-chiral liquid crystal composition and had a crystal-smectic C phase transition point (C-SC point) of 4° C., a smectic C phase-smectic A phase transition point (SC-SA point) of 65° C., a smectic A phase-nematic phase transition point (SA-N point) of 79° C., and a nematic phase-isotropic phase transition point (N-I point) of 90° C.

Composition B comprising 80% of Composition A and 20% of the compound of Example 10 having formula:

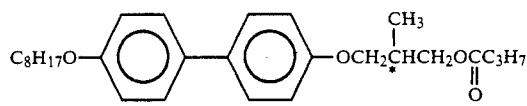

was a chiral smectic liquid crystal composition and had a chiral smectic C phase-smectic A phase transition point (SC*-SA point) of 58° C., a smectic A phase-cholesteric phase transition point (SA-Ch point) of 71.5° C., and a cholesteric phase-isotropic phase transition point (Ch-I point) of 79° C.

Composition B was introduced in a 2 μm thick cell equipped with transparent electrodes, which had been coated with polyvinyl alcohol as an aligning agent and had been subjected to parallel aligning treatment by rubbing the surface thereof, to thereby produce a liquid crystal display element. This element was placed between two polarizers crossed at right angles, and an electric field was applied thereto. Upon application of ±10 V, a change in transmission light intensity was observed. The response time was determined from the change in transmission light intensity, and the PS was determined according to a Sowyer-Tower method. The results obtained are shown in Table 2 below.

TABLE 2

| Temperature (°C.) | Response Time (μsec) | PS (nC/cm$^2$) |
|---|---|---|
| 55 | 78 | 1.4 |
| 45 | 110 | 2.4 |
| 35 | 150 | 3.3 |
| 25 | 250 | 3.8 |

As can be seen from the Table, use of the compound according to the present invention in a nonchiral smectic composition provides a satisfactory ferroelectric liquid crystal composition showing spontaneous polarization.

EXAMPLE 12 (COMPOSITION 7)

A nematic liquid crystal composition having the following formulation was prepared.

Formulation

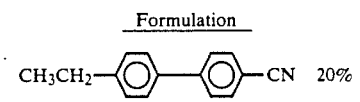 20%

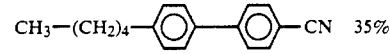 35%

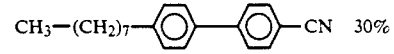 30%

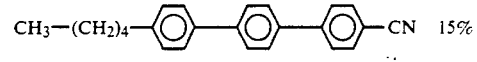 15%

The composition was introduced in a cell with transparent electrodes, the distance between the electrodes being 10 μm, which had been coated with polyvinyl alcohol as an aligning agent and had been subjected to parallel aligning treatment by rubbing the surface thereof, to thereby produce a TN type liquid crystal display element. Observation of the element under a polarization microscope showed that reverse twist domains were formed.

The compound of Example 10 was added to the above nematic liquid crystal composition in an amount of 1%. The resulting composition was introduced in the same cell as used above and observed as a TN type liquid crystal display element in the same manner as above. It was confirmed that the reverse twist domain disappeared, and a uniform nematic phase was observed.

EXAMPLE 13 (COMPOSITION 8)

A chiral nematic liquid crystal composition was prepared by adding 1% of the compound of Example 10 to ZLI-1132 (a trade name of a nematic liquid crystal composition on the market, produced by Merck & Co.), and its chiral pitch was measured by a Cano wedge method. As can be seen from the results shown in Table 3 below, the temperature dependence of the chiral pitch was small.

TABLE 3

| Temperature (°C.) | Pitch (μm) |
|---|---|
| 20 | 29.6 |
| 30 | 31.0 |
| 40 | 32.6 |
| 50 | 34.4 |
| 60 | 36.4 |

While the invention has been described in detail and with reference to specific embodiments thereof, it will be apparent to one skilled in the art that various changes and modifications can be made therein without departing from the spirit and scope thereof.

We claim:

1. A compound expressed by the formula

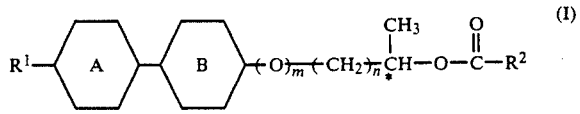 (I)

wherein
R¹ represents an alkyl group or alkoxy group each of 1 to 12 carbon atoms;
R² represents a linear or methyl-branched alkyl group of 1 to 15 carbon atoms;

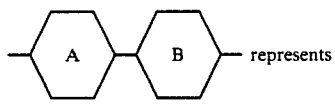 represents

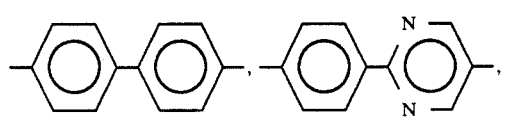

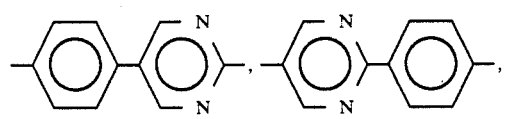

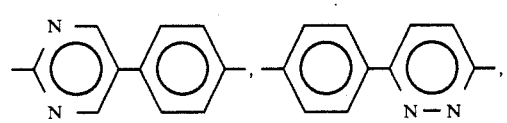

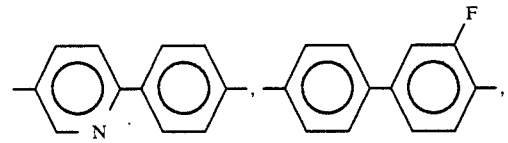

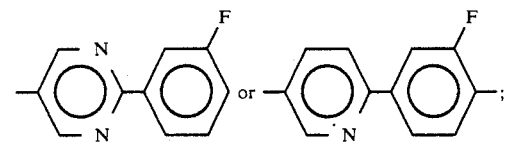

m is 0 to 1;
n is 1, 2 or 3;
and the symbol * indicates that the carbon atom onto which the symbol * is attached is an asymmetric carbon atom.

2. A compound according to claim 1, wherein said R² is an alkyl group of 1 to 10 carbon atoms, said

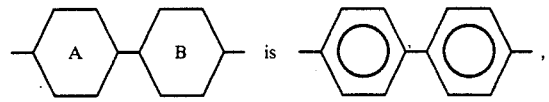

said m is 1 and said n is 1.

3. A compound according to claim 1, wherein said R² is an alkyl group of 1 to 10 carbon atoms, said

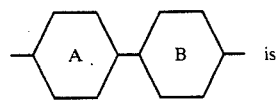 is

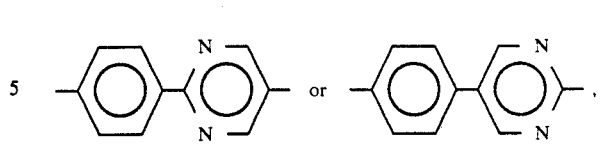

said m is 1 and said n is 1.

4. A compound according to claim 1, wherein said R² is an alkyl group of 1 to 10 carbon atoms, said

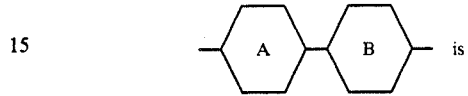 is

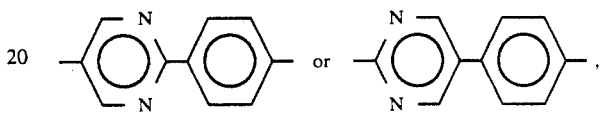

said m is 1 and said n is 1.

5. A compound according to claim 1, wherein said R² is an alkyl group 1 to 10 carbon atoms, said

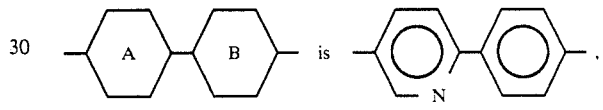

said m is 1 and said n is 1.

6. A compound according to claim 1, wherein said R² is an alkyl group of 1 to 10 carbon atoms, said

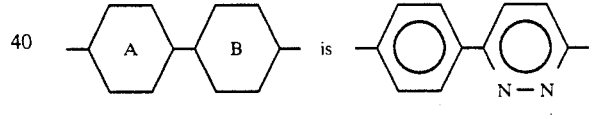

said m is 1 and said n is 1.

7. A compound according to claim 1, wherein said R² is an alkyl group of 1 to 10 carbon atoms, said

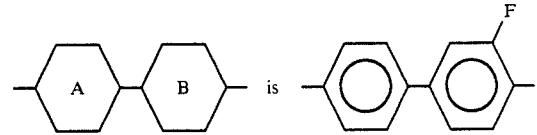

said m is 1 and said n is 1.

8. A compound according to claim 1, wherein said R² is an alkyl group of 1 to 10 carbon atoms, said

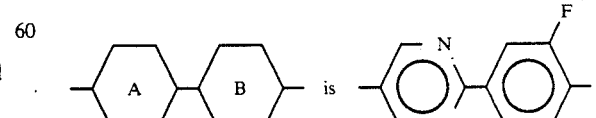

said m is 1 and said n is 1.

9. A compound according to claim 1, wherein said R² is an alkyl group of 1 to 10 carbon atoms, said

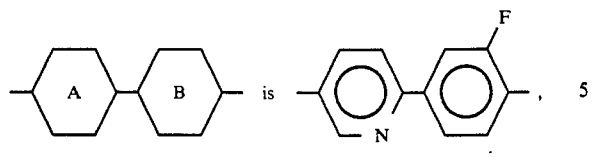

said m is 1 and said n is 1.

10. A compound according to claim 1, wherein said R² is an alkyl group of 1 to 10 carbon atoms, said

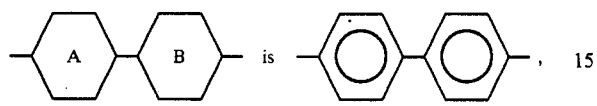

said m is 1 and said n is 2.

11. A compound according to claim 1, wherein said R² is an alkyl group of 1 to 10 carbon atoms, said

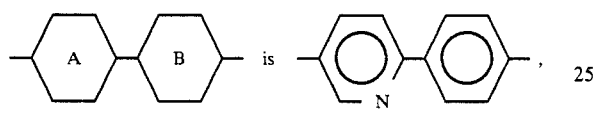

said m is 1 and said n is 2.

12. A compound according to claim 1, wherein said R² is an alkyl group of 1 to 10 carbon atoms, said

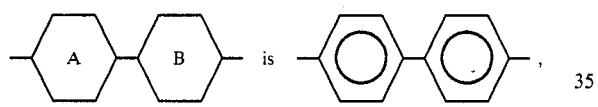

said m is 0 and said n is 1.

13. A compound according to claim 1, wherein said R² is an alkyl group of 1 to 10 carbon atoms, said

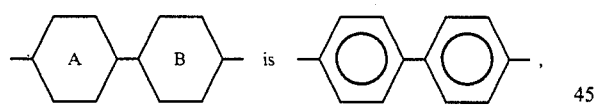

said m is 0 and said n is 2.

14. A compound according to claim 1, wherein said R² is an alkyl group of 1 to 10 carbon atoms, said

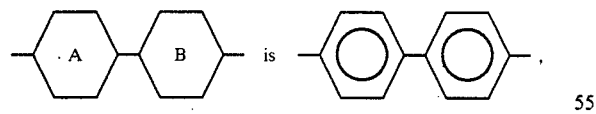

said m is 0 and said n is 3.

15. A compound according to claim 2, wherein R¹ is an alkyl group of 1 to 12 carbon atoms.

16. A compound according to claim 2, wherein R¹ is an alkoxy group of 1 to 12 carbon atoms.

17. A liquid crystal composition comprising at least two components at least one of which is a compound expressed by the formula (I) of claim 1.

18. A liquid crystal composition according to claim 17 which exhibits a chiral smectic phase.

19. A liquid crystal composition according to claim 17 which exhibits a chiral nematic phase.

20. A light-switching element containing a liquid crystal composition of claim 17.

21. A compound represented by the formula:

$$R^{1'}-A-B-O-CH_2\overset{CH_3}{\underset{*}{C}}HCH_2-O-\overset{O}{\underset{\|}{C}}-R^{2'''} \quad (I'')$$

wherein R¹' represents a striaght chain alkyl or alkoxy group, each of 7 to 10 carbon atoms, R²''' represents a straight chain alkyl group of 3 to 14 carbon atoms, or an optically active alkyl group of 4 to 14 carbon atoms having a methyl branch, carbon —A—B— represents

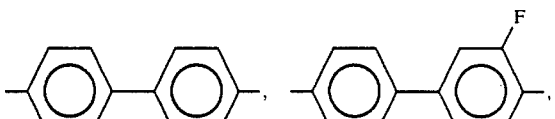

and the asterisk mark * indicates that the carbon atom provided with * is an asymmetrical carbon atom.

22. A compound according to claim 21, wherein —A—B— is

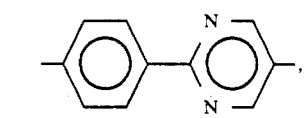

23. A compound according to claim 21, wherein —A—B— is

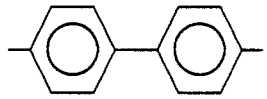

24. A compound according to claim 21, wherein —A—B— is

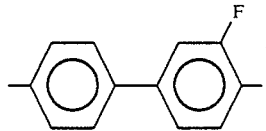

25. A compound according to claim 21, wherein —A—B— is

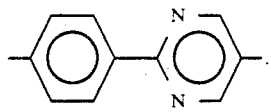

26. A compound according to claim 21, wherein —A—B— is

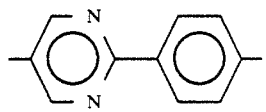

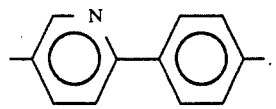
27. A compound according to claim 21, wherein $R^{1'}$ is a straight chain alkyl group of 7 to 10 carbon atoms.
28. A compound according to claim 21, wherein $R^{2''}$ is a straight chain alkyl group of 3 to 14 carbon atoms.
29. A liquid crystal composition comprising at least two components at least one of which is a compound of formula (I'') as set forth in claim 21.
* * * * *